US00PP28153P3

(12) United States Plant Patent
Yamada

(10) Patent No.: US PP28,153 P3
(45) Date of Patent: Jul. 4, 2017

(54) *CATHARANTHUS* PLANT NAMED 'SUNCATHA 2335'

(50) Latin Name: *Catharanthus roseus*
Varietal Denomination: Suncatha 2335

(71) Applicant: SUNTORY FLOWERS LIMITED, Tokyo (JP)

(72) Inventor: Masahiro Yamada, Kanagawa (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 312 days.

(21) Appl. No.: 14/121,583

(22) Filed: Sep. 19, 2014

(65) Prior Publication Data

US 2015/0089698 P1 Mar. 26, 2015

Related U.S. Application Data

(60) Provisional application No. 61/960,551, filed on Sep. 20, 2013.

(51) Int. Cl.
*A01H 5/02* (2006.01)

(52) U.S. Cl.
USPC ..... Plt./263.1
CPC ..... *A01H 5/02* (2013.01)

(58) Field of Classification Search
USPC ..... Plt./263.1, 226
CPC ..... A01H 5/02; A01H 5/00
See application file for complete search history.

(56) References Cited

PUBLICATIONS

"2012 Spring-Summer gardening catalog," Daiichi Engei Co., Ltd., Oct. 2011, pp. 20-21.
Registration No. 21647, Registration date Mar. 19, 2012, Suntory Flowers Company, 1 page.

*Primary Examiner* — Kent L Bell
(74) *Attorney, Agent, or Firm* — Kilpatrick Townsend & Stockton LLP

(57) ABSTRACT

Disclosed herein is a new and distinct variety of *Catharanthus* plant having vigorous, upright plant habit, abundant branching, especially basally branching, developed from the base of the plant throughout the growing season and great profusion of double, bright red purple flowers.

2 Drawing Sheets

Botanical designation: *Catharanthus roseus.*
Cultivar denomination: 'Suncatha 2335'.

BACKGROUND OF THE INVENTION

The present invention relates to a new and distinct variety of *Catharanthus* plant, which is hereinafter referred to by the name of 'Suncatha 2335'.

*Catharanthus roseus*, which is also known as *Vinca rosea*, is a very popular plant that is used for flower bedding and potting in the summer and autumn season.

The purpose of this invention is to obtain a new *Catharanthus* cultivar having vigorous, upright plant characteristics, abundant branching, especially basally branching, developed from the base of the plant throughout the growing season and great profusion of double, bright red purple flowers, the entire bush remaining in bloom for a considerable period of time.

The new *Catharanthus* plant was originated from a cross-pollination of the female parent 'S22-P-5' and the male parent 'Daiichi-SIR22-16'. The female parent 'S22-P-5' (unpatented) used in the crossing of 'Suncatha 2335' is a strain of applicant's breeding lines (i.e., proprietary *Catharanthus roseus* selection), having pale pink petals, and the male parent 'Daiichi-SIR22-16' used in the crossing of 'Suncatha 2335' is a strain of applicant's breeding lines (i.e., proprietary *Catharanthus roseus* selection), having red single petals, which was applied for Japanese plant variety protection (the application number: 25152; the application date: 2010 Aug. 31; the registration number: 21647; the registration date: 2012 Mar. 19). The cross-pollination was conducted in Sep. 10, 2010 at Yame-gun, Fukuoka, Japan.

In February 2012, the seedlings obtained by the crossing were planted in field, and some seedlings were selected in view of growth habit, flower size and color thereof. In August 2012, the stem tip culturing was carried out, and then the propagation was started.

In July 2013, the cultivation of the seedlings was repeated. The botanical characteristics of that plant were then examined, using similar varieties 'Daiichi-S23-25' and 'Daiichi-SIR22-16' for comparison. As a result, it was concluded that this *Catharanthus* plant is distinguishable from any other variety, whose existence is currently known, and is uniform and stable in its characteristics.

The new variety of *Catharanthus roseus* plant is named 'Suncatha 2335'.

SUMMARY OF THE INVENTION

This new variety is unlike any *Catharanthus* plants commercially available as evidenced by the following unique combinations of characteristics.

1. Vigorous, upright plant characteristics.
2. Abundant branching, especially basally branching, developed from the base of the plant throughout the growing season.

3. Great profusion of double, bright red purple flowers, the entire bush remaining in bloom for a considerable period of time.

The new variety 'Suncatha 2335' differs from the similar variety 'Daiichi-S23-25', which was applied for Japanese plant variety protection (the application number: 27372; the application date: Sep. 3, 2012; the registration number 23254; the registration date: Mar. 12, 2014), in the following points.

1. The main color of surface of corolla lobe of 'Suncatha 2335' is bright red purple (RHS N66C). That of 'Daiichi-S23-25' is PURPLE-VIOLET (RHS near N80A).

The new variety 'Suncatha 2335' differs from the similar variety 'Daiichi-SIR22-16', which was applied for Japanese plant variety protection (the application number: 25152; the application date: 2010 Aug. 31; the registration number 21647; the registration date: Mar. 19, 2012), in the following points.

1. The main color of surface of corolla lobe of 'Suncatha 2335' is bright red purple (RHS N66C). That of 'Daiichi-SIR22-16' is white (RHS NN155C).
2. The leaf size (L×W) of 'Suncatha 2335' is 49 mm×23 mm. That of 'Daiichi-SIR22-16' is 45 mm×28 mm.
3. The petiole length of 'Suncatha 2335' is 10.5 mm. That of 'Daiichi-SIR22-16' is 7.0 mm.

This new variety of *Catharanthus* plant 'Suncatha 2335' was asexially reproduced by the use of cuttings at Higashiomi, Shiga, Japan, and homogeneity and stability thereof were confirmed. The instant plant retains its distinctive characteristics and produces true to type in successive generations.

BRIEF DESCRIPTION OF THE PHOTOGRAPHS

The depicted plants had been reproduced by the use of cuttings and were photographed during October 2013 while growing outdoors in wall pots with about 15 cm of container size at an age of approximately 6 months.

The second sheet is a photograph of a typical plant of the new variety of *Catharanthus* plant 'Suncatha 2335' while growing in a pot.

The first sheet is a photograph of a close view of flowers of the new variety of *Catharanthus* plant 'Suncatha 2335'.

DETAILED BOTANICAL DESCRIPTION

In October 2013, the cultivation of the seedlings was repeated at Higashiomi, Shiga, Japan. The average day temperature was about 25° C., and the average night temperature was about 15° C. The plants were grown under natural sunlight. The number of days to flowering (response time) was about 3 to 4 weeks. The keeping quality was about 180 days. The plants had temperature resistance to about 5° C. (the lowest temperature) and about 35 to 40° C. (the highest temperature). Further, the plants had the same tolerance to pests and pathogens as a typical *Catharanthus* plant.

For the parentage information: The female parent 'S22-P-5' (unpatented) used in the crossing of 'Suncatha 2335' is a strain of applicant's breeding lines (i.e., proprietary *Catharanthus roseus* selection), having pale pink petals, and the male parent 'Daiichi-SIR22-16' used in the crossing of 'Suncatha 2335' is a strain of applicant's breeding lines (i.e., proprietary *Catharanthus roseus* selection), having red single petals, which was applied for Japanese plant variety protection (the application number: 25152; the application date: Aug. 31, 2010; the registration number: 21647; the registration date: Mar. 19, 2012).

For the propagation information: the new cultivar was propagated by cutting; the number of days to initiate roots during the summer was about two weeks; approximate soil and/or air temperature during the summer was around 30° C.; the number of days to initiate roots during the winter was about three weeks; approximate soil and/or air temperature during the winter was around 25° C.; the number of days to produce a rooted young plant during the summer was about five weeks; the number of days to produce a rooted young plant during the winter was about six weeks; root density was moderate; root branching was free; root color was white; and root texture was fibrous.

The botanical characteristics of the new and distinct variety of *Catharanthus* plant named 'Suncatha 2335' at an age of approximately 4 months are shown in the following Table. In the following description, the color-coding is in accordance with the Horticultural Colour Chart of The Royal Horticultural Society, London, England (R.H.S. Colour Chart The 5th edition 2007).

PLANT VARIETY DESCRIPTION

| CHARACTERISTIC | APPLICATION VARIETY Suncatha 2335 |
|---|---|
| ANNUAL, BIENNIAL or PERENNIAL? | Grown as annual |
| TYPE OF PLANT: i.e., TREE, SHRUB, SUBSHRUB, VINE, CUT FLOWER, POTTED PLANT | Potted plant |
| APPROPRIATE CONTAINERS +/or CROPPING SYSTEM | Ideal for pots, hanging baskets. |
| GROWTH HABIT | Upright |
| PLANT HEIGHT | About 22.0 cm |
| PLANT DIAMETER OR AREA OF SPREAD | About 25.0 cm |
| PLANT VIGOR | Vigorous |
| BRANCHING HABIT | Freely branching |
| BASAL BRANCHING? | Present |
| PINCHING REQUIRED? | Not required. |
| NUMBER OF LATERAL BRANCHES | About 7 |
| NUMBER OF SECONDARY LATERAL BRANCHES | About 2 |
| LATERAL BRANCH LENGTH | About 20.5 cm |
| LATERAL BRANCH DIAMETER | About 4.3 mm |
| INTERNODE LENGTH | About 22.5 mm |
| STEM ASPECT | Upright to outward |
| RHS Near 142C | |
| STEM COLOR (and bark color, if applicable) | Upper: with anthocyanin pigmentation colored 182B |
| STEM COLOR (if any) | RHS Near 182B |
| STEM PUBESCENCE | Present, few |
| OTHER PLANT/STEM CHARICTERISTICS— | |
| LEAF ARRANGEMENT | Opposite |
| COMPOUND OR SIMPLE? | Simple |
| QUANTITY OF LEAVES PER LATERAL BRANCH | About 12 |
| LEAF (LEAFLET) SHAPE | Narrow elliptic |
| LEAF (LEAFLET) TIP | Acute |
| LEAF (LEAFLET) BASE | Obtuse |
| LEAF LENGTH | About 49.1 mm |
| LEAF WIDTH | About 23.0 mm |
| LEAF THICKNESS | About 0.3 mm |
| LEAF (LEAFLET) TEXTURE | Pubescent, both sides |
| LEAF PUBESCENCE? | Present |
| LEAF (LEAFLET) MARGIN | Entire |
| VENATION PATTERN | Reticulate venation |
| LEAF COLOR, YOUNG, UPPER SIDE | RHS Near 137A |
| LEAF COLOR, YOUNG, UNDER SIDE | RHS Near 137D |
| LEAF COLOR, MATURE, UPPER SIDE | RHS Near141B~143B |
| LEAF COLOR, MATURE, UNDER SIDE | RHS Near N137C |
| VENATION COLOR, UPPER SIDE | RHS Near 137C |

-continued

| PLANT VARIETY DESCRIPTION | |
|---|---|
| CHARACTERISTIC | APPLICATION VARIETY Suncatha 2335 |
| VENATION COLOR, UNDER SIDE | RHS Near 142D |
| VARIEGATION? | Absent |
| PETIOLE? | Present |
| PETIOLE LENGTH | About 10.5 mm |
| PETIOLE DIAMETER | About 3.3 mm |
| PETIOLE TEXTURE | Pubescent |
| PETIOLE COLOR | RHS Near 182A |
| OTHER FOLIAGE CHARACTERISTICS | — |
| FLOWER ARRANGEMENT | Borne in upper leaf axils. |
| INFLORESCENCE TYPE OR FORM (if applicable) | Solitary |
| QUANTITY OF FLOWERS PER PLANT | About 40 |
| FLOWER TYPE or FORM | Double |
| FLOWERING HABIT | Continuously |
| NATURAL FLOWERING SEASON | Early summer to late autumn |
| TIME TO FLOWER OR RESPONSE TIME | About 2~3 weeks |
| FRAGRANCE | Absent |
| FLOWER BUD LENGTH | About 38.9 mm |
| FLOWER BUD DIAMETER | About 6.9 mm |
| FLOWER BUD SHAPE | Clavate |
| FLOWER BUD COLOR | RHS Naer 65D |
| FLOWER ASPECT; i.e., UPRIGHT, OUTWARD, DROOPING, etc. | Upright |
| FLOWER PARACOROLLA | Present |
| FLOWER DIAMETER | About 43.4 mm |
| FLOWER DEPTH (HEIGHT) | About 43.6 mm |
| FLOWER LONGEVITY ON PLANT | About 2~3 days |
| PERSISTENT OR SELF-CLEANING? | Not persistent. |
| PETAL TEXTURE, UPPER SURFACE | Smooth |
| PETAL TEXTURE, LOWER SURFACE | Smooth |
| TUBE TEXTURE | Smooth, pubescent |
| PETAL ARRANGEMENT | Free |
| PETAL NUMBER | 10, Double |
| PETALS FUSED? | Fused |
| PETAL SHAPE | Outside: Oblanceolate<br>Inside: Obtrullate |
| PETAL MARGIN | Absent or very weak |
| ASYMMETRY OR SYMMETRY | Outside: Asymmetry<br>Inside: Symmetry |
| PETAL TIP | Mucronate |
| PETAL BASE | Fused |
| PETAL LENGTH | Outside: about 24.9 mm<br>Inside: about 20.1 mm |
| PETAL WIDTH | Outside: about 16.5 mm<br>Inside: about 10.0 mm |
| NUMBER OF PETAL COLOR, UPPER SIDE (EXCEPT FLOWER EYE) | 1 |
| PETAL COLOR , WHEN OPENING, UPPERSIDE | RHS Near N57C |
| PETAL COLOR , WHEN OPENING, LOWERSIDE | RHS Near 65C |
| PETAL COLOR, FULLY OPENED, UPPERSIDE | RHS Near N66C |
| PETAL COLOR, FULLY OPENED, LOWERSIDE | Petal tip: RHS Near 65A~65C |
| FLOWER EYE | Present |
| FlOWER EYE DIAMETER | About 4.0 mm |
| FlOWER EYE COLOR | RHS Near 60B |
| RECEPTACLE | Absent |
| RECEPTACLE COLOR | — |
| TUBE DIAMETER | About 1.7 mm |

-continued

| PLANT VARIETY DESCRIPTION | |
|---|---|
| CHARACTERISTIC | APPLICATION VARIETY Suncatha 2335 |
| TUBE LENGTH | About 25.1 mm |
| THROAT COLOR(inside) | RHS Near 145B~145D |
| TUBE COLOR(outside) | RHS Near 145A~145B<br>Base: with anthocyanin pigmentation colored 181C |
| SEPAL ARRANGEMENT | Single whorl |
| NUMBER OF SEPALS | 5 |
| SEPAL SHAPE | Linear-triangular |
| SEPAL MARGIN | Entire |
| SEPAL TIP | Acute |
| SEPAL BASE | Fused |
| SEPAL LENGTH | About 2.9 mm |
| SEPAL WIDTH | About 0.9 mm |
| SEPAL COLOR,IMMATURE, UPPER SIDE | RHS Near 144B |
| SEPAL COLOR,IMMATURE, UNDER SIDE | RHS Near 144B |
| SEPAL COLOR,MATURE, UPPER SIDE | RHS Near 144B |
| SEPAL COLOR,MATURE, UNDER SIDE | RHS Near 144B |
| CALYX SHAPE | Star shape |
| CALYX LENGTH | About 3.8 mm |
| CALYX DIAMETER | About 4.8 mm |
| PEDUNCLE LENGTH | About 3.4 mm |
| PEDUNCLE DIAMETER | About 1.8 mm |
| PEDUNCLE ANGLE | Upright, slanting above |
| PEDUNCLE TEXTURE | Smooth |
| PEDUNCLE COLOR | RHS Near 144B |
| STAMEN NUMBER | 5 |
| STAMEN LENGTH | About 3.1 mm |
| ANTHER SHAPE | Narrow elliptic |
| ANTHER SIZE | (L) About 2.9 mm |
| ANTHER SIZE | (W) About 1.2 mm |
| ANTHER COLOR | RHS Near 8C |
| AMOUNT OF POLLEN | Few |
| POLLEN COLOR | RHS Near 8D |
| PISTIL NUMBER | 1 |
| PISTIL LENGTH | About 20.8 mm |
| STIGMA SHAPE | Transversely ellipsoidal |
| STIGMA COLOR | RHS Near 145A |
| STYLE COLOR | RHS Near 145C |
| OVARY COLOR | RHS Near 145B |
| OTHER FLOWER CHARACTERISTICS | — |
| QUANTITY OF SEEDS | Seeds production has not been observed. |
| ROOT STRUCTURES such as BULBS, CORMS or RHIZOMES? | Fibrous root |
| LOW TEMPERATURE TOLERANCE | Around 5° C. |
| HIGH TEMPERATURE TOLERANCE | Around 35° C.~40° C. |
| DISEASE RESISTANCE AND/OR SUSCEPTIBILITY | Normal |
| RESISTANCE OF PESTS AND/OR SUSCEPTIBILITY | Normal |

This new variety of *Catharanthus* plant having the above botanical characteristics is suitable for flower bedding and potting, particularly in hanging pots or planters.

What is claimed:

1. A new and distinct variety of *Catharanthus* plant named 'Suncatha 2335', substantially as herein illustrated and described.

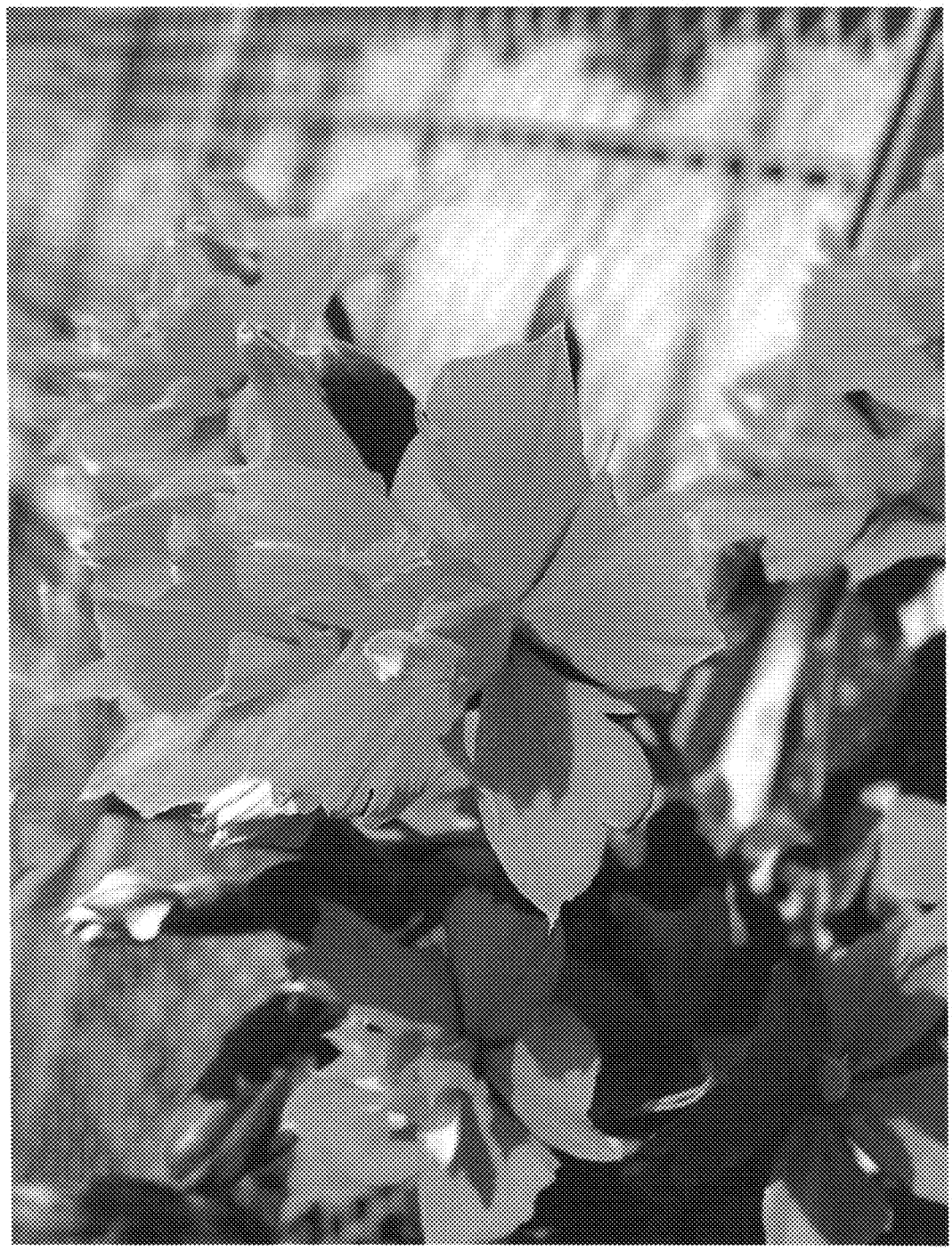

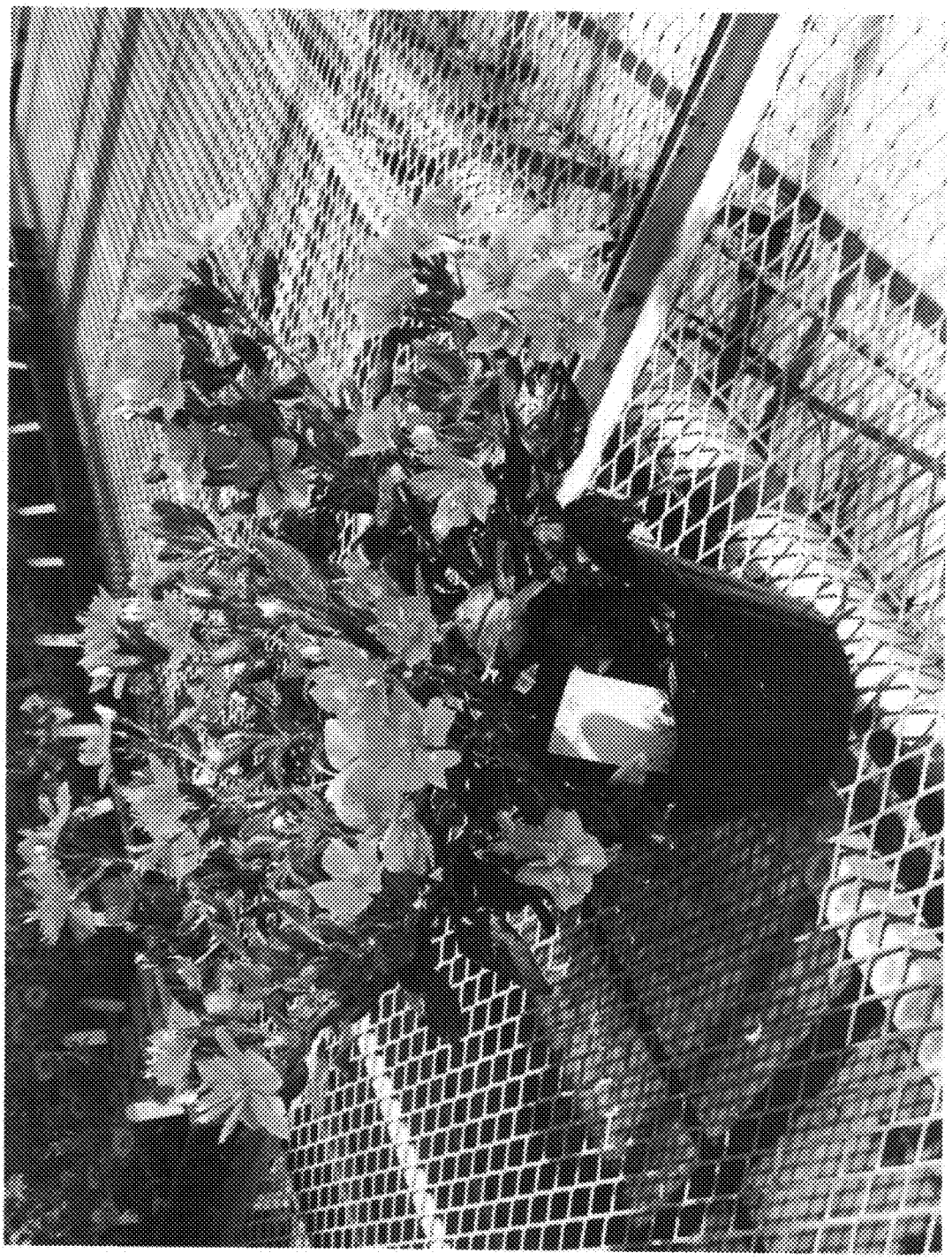

* * * * *